US006713027B2

United States Patent
McNulty, Jr.

(10) Patent No.: US 6,713,027 B2
(45) Date of Patent: Mar. 30, 2004

(54) OZONATOR FOR STERILIZING, DECONTAMINATING, DISINFECTING, AND/OR SANITIZING SURGICAL INSTRUMENTS

(75) Inventor: James F. McNulty, Jr., Calimesa, CA (US)

(73) Assignee: Electroclave, Newport Beach, CA (US)

( * ) Notice: Subject to any disclaimer, the term of this patent is extended or adjusted under 35 U.S.C. 154(b) by 154 days.

(21) Appl. No.: 09/939,169

(22) Filed: Aug. 24, 2001

(65) Prior Publication Data

US 2003/0121770 A1 Jul. 3, 2003

(51) Int. Cl.[7] ................................................. B01J 19/08
(52) U.S. Cl. ............................ 422/186.06; 422/186.07; 422/186.15
(58) Field of Search ..................... 422/186.06, 186.07, 422/186.15

(56) References Cited

U.S. PATENT DOCUMENTS 6,007,770 A * 12/1999 Peiper et al. ................. 422/22

* cited by examiner

Primary Examiner—Kishor Mayekar
(74) Attorney, Agent, or Firm—Leonard Tachner

(57) ABSTRACT

An apparatus and method for the use of ozone as a sterilant for many classes of surgical instruments which are at least partially metallic. Three features are the connection of a voltage carrying part of the instrument to be sterilized as the electrode of an ozone generating cell, which employs a glow discharge and maintaining the temperature of this electrode below 500° C., and that no solid dielectric exists between opposed electrodes in the ozone generating cell. Ozone is thereby localized about voltage carrying and any non-voltage carrying parts of the electrode connected instrument. The control of electrode heating helps to maintain the increasing atmospheric concentration of the ozone, which will however eventually reach a natural limit. Local heating of the electrode configuration is controlled where the instrument to be sterilized is connected at least periodically as the negative electrode.

7 Claims, 8 Drawing Sheets

OZONATOR FOR STERILIZING, DECONTAMINATING, DISINFECTING, AND/OR SANITIZING SURGICAL INSTRUMENTS

BACKGROUND OF THE INVENTION

1. Field of the Invention

The present invention pertains generally to apparatus for sterilization of objects such as dental instruments and more particularly to such sterilization using ozone generation.

2. Background Art

Unlike sanitizing or disinfection, where certain contaminants can be selectively destroyed, sterilization requires that the viability of not some, but rather all, living contaminants is destroyed. The use of ozone treatment and ozonators to disinfect and sanitize is not per se unique. Both have a long history of use for these purposes. Ozone is used to purify drinking water, disinfect bottled water, treat industrial waste, deodorize air and sewage gases, and to further extend the life of perishables preserved by cold storage (ozone remains a strong disinfectant even at temperatures below $-150°$ F.). However, hitherto, the complete sterilization of surgical instruments has not been achieved through ozone treatment.

Ozone, $O_3$, or triatomic oxygen is a naturally occurring molecule. It is produced in the low pressure stratas of earth's atmosphere as the result of the action of ultra violet radiation upon the $O_2$ molecule and, otherwise, as the result of electrical discharges which naturally occur in the earth's atmosphere. $O_2$, the more stable molecular form of oxygen, is split into atomic oxygen when bombarded with either electrons or electromagnetic radiation, like UV light, having energy sufficient to split the O to O double bond of $O_2$ (6 eV to 7 eV). The highly reactive single atomic oxygens then bond with other $O_2$ molecules to form $O_3$ ($3O_2(g)$+Energy= $2O_3(g)$). Near the Earth's surface the concentration of this trivalent oxygen molecule in rural atmosphere is usually about 0.002–0.003 PPM (parts per million).

The German chemist Christian Friedrich Schonbein first discovered $O_3$ in 1839. He named the molecule ozone, from the Greek ozein "to smell", as ozone has a readily identifiable acrid odor which can be recognized by olfaction at fewer than 0.015 PPM in atmosphere and becomes rather unpleasant above 0.1 PPM in atmosphere. It appears as a bluish hue at 5 PPM in atmosphere.

With the validation of the germ theory of disease, after Pasteur's ground breaking U tube experiments reported in the *Annales des Sciences Naturelles,* 4th series, Vol. 16 (1861), the germicidal action of ozone was quickly recognized. $O_3$ is a highly unstable molecule, which readily reacts with other matter to form $O_2$ by losing one of its constituent atomic oxygens to the reaction. Both $O_3$ and O are highly reactive. Both have oxidizing potentials which are greater than that of hypochlorous acid, a bleaching and chlorinating agent and disinfectant, which itself is recognized as a very strong oxidizing agent. The germicidal power of Cl (chlorine) is dependent upon the release of free hypochlorous acid. Yet, the oxidizing potential of HClO is only 1.36 V. The oxiding potential of O is 2.07 V. The oxidizing potential $O_3$ is 1.67 V. $O_3$ is second only to F (fluorine) and O in electronegative oxidation potential, with F being the most electronegative of the elements on the Pauling Scale.

$O_3$ is highly reactive with hydrocarbons and other unsaturated molecules. On contact, this strong oxidant reacts with the hydrophobic fatty acid tails of the phospholipids which form the phospholipid bilayer of bacterial cell membranes. This chemical reaction cleaves the double bonds in these unsaturated fatty acids. This, in turn, alters cell permeability, thus lysing the cells and, thereby, achieving a bactericidal effect. $O_3$ also cleaves the double bonds in the functional groups of the polypeptide chains forming the protein capsids of viruses, thus compromising these barriers and, thereby, achieving a biocidal effect. $O_3$ is proved to kill on contact pathogenic bacteria of the genuses Escherichia (meningitis), Salmonellas (typhoid fever), Legionella (Legionnaire's disease), Streptococcus (bacterial pneumonia, septicemia, endocarditis, scarlet fever) Vibrio (cholera), influenza viruses, polio viruses, various fungi and other parasites, like the amoebas and other protozoans and their cysts (malaria, sleeping sickness), including crypto sporidium. $O_3$ is known to kill parasites as large as nematodes or round worms, including enterobius vermicularis (pin worms) and *Trichinella spiralis* (trichinosis). $O_3$ eliminates pathogenic bacteria and viruses from water 3,125 times more rapidly than Cl (chlorine). Moreover, unlike Cl, $O_3$ does not leave carcinogenic residues that impart a characteristically unpleasant taste and odor to the water.

The city of Nice, France built the first plant for purifying municipal water supplies by ozonation in 1906. Some 2000 such water treatment plants now exist worldwide. They are particularly common in land scarce Western Europe where unlike in the U.S., large acreages are not available for the simpler and less costly sand filtration of waste water during its tertiary treatment for reuse as potable supply. The first ozone plant to control sewage odors was built in New York City in the 1930's.

The basic problem with achieving the sterilization of objects through ozone treatment is no different than the basic problem with achieving sterilization through other antimicrobial agents like moist heat, dry heat, ethylene oxide (normally mixed with $CO_2$ or rare gases to minimize explosion hazard) and other gases, and liquid chemicals. The problem is one of distribution. To be a steriliant, the agent must be distributed in lethal quantity to all inoculum on the object to be sterilized. In limited circumstance, this problem has been overcome with moist and dry heat and ethylene oxide gas.

For example, moist heat at $250°$ F. will kill even the hardy *B.stearothermopilus* endospores in less than 1 hour. The destruction of these heat resistant spores is a gold standard for evaluating the effectiveness of heat sterilizers. If these endospores, the most heat resistant of all known microbes are killed, it can be assumed that all other bacteria and the much smaller viruses (including HIV and Hepatitis) are also dead. Given sufficient time, continuously generated moist heat will distribute to all inoculum by forced convection and thermal conduction. With steam, these distribution methods are aided by condensation and release of the latent heat of vaporization. Steam with a temperature of at least $250°$ F. can be generated under pressure in an autoclave. After approximately 30 minutes, heat from the $250°$ F. pressurized steam will distribute to all inoculum on an oven's contents, including *B.Stearothermopolis* endospores, and kill them. After several hours, often overnight treatment, the sporicidal chemical ethylene oxide gas, sometimes under pressure and/or at slightly elevated temperature ($120°$ F. to $140°$ F.), will distribute to all inoculum on a chamber's contents, including *B.Stearothermopolis* endospores, and kill them.

The problem with distributing ozone to sterilize has not been so easy to resolve, even in limited circumstances. This highly unstable molecule quickly breaks down in atmosphere to form $O_2$. $O_3$ is subject to unimolecular reaction. An ozone molecule $O_3$, which is energetically excited by, for example, molecular collision, absorbing a photon, or heating, spontaneously decomposes to dioxygen and atomic oxygen. At room temperature, surface reactions appear most responsible for the decomposition of $O_3$. The half life of the $O_3$ molecule, even in dry atmosphere, is a mere 20 to 100 minutes, normally about 30 minutes, and this short half life is quite adversely affected by moderately increased temperature and humidity. Thermal decomposition of $O_3$ has been extensively studied within a range of 80–500° C. $O_3(g)$ rapidly decomposes at temperatures above 100° C. As little as 0.02–0.03 mg $H_2O$ per liter of air impairs $O_3$ yields. The presence of water vapor in an ozone generating cell stimulates the production of nitric acid $HNO_3$ in lieu of $O_3$, thereby, decreasing $O_3$ production. $HNO_3$ is not itself as effective an oxidizing and, therefore, germicidal agent as $O_3$. $HNO_3$ is also a strong corrosive. Therefore, the presence of significant $HNO_3$ in the ozone generating cell is not desirable. $HNO_3$ will corrode generation cell components. Water vapor also provides alternative reactants for any $O_3$ produced, thus decreasing both its half life and biocidal effect by volume. Catalyzed by the hydroxyl ion, $O_3$ decomposition occurs much more rapidly in aqueous solution than in dry air. $O_3$, therefore cannot be stored and must be generated very close to its point of application.

$O_3$ has hitherto remained unperfected as the sterilant for any object. Commercial ozonators (or ozonizers) use one of two methods to produce ozone. Air or O under pressure is passed by an ultraviolet lamp or, alternatively, by the corona discharge method where air or O under pressure (usually 1.2 to 2 atm) is passed between electrode plates (normally screen plates) and through a glow discharge, occurring typically at a tension of between 7,000 to 20,000 VAC. With either method, the ozonated air is then forced by pressure differential to transport its $O_3$ from the ozonator and hopefully into contact with pathogenic microbes. While producing a sanitizing effect, this diffusion of the ozone is unlikely to result in $O_3$ contact sufficient to actually sterilize contaminated objects within fluids.

All heretofore "perfected" methods of sterilization have also had their own problems. The two main disadvantages with these sterilants have been heat and/or time.

While autoclaving is the most versatile of these methods, many materials and instruments still suffer irreversible damage when exposed to moist heat at the temperatures and for the times required for sterilization. After several sterilization cycles, moist heat shortens the useful life of most garments and other tools. After as few as 4 autoclave cycles, rubber goods like gloves rapidly loose tensile strength. Undetected rupture of these prophylactic barriers to infection could have catastrophic consequences for the health care workers who depend upon them for protection. Moist heat sterilization rapidly corrodes metal instruments and dulls blades. Overloaded autoclaves or super heated steams may not sterilize at all. In these cases, steam sterilization does little more than help to distribute pathogenic microbes. Steam under pressure may not penetrate the lubricating jellies frequently used in surgical theaters. Autoclaving, the most versatile method of sterilization, is still unsuitable as a method for sterilizing anhydrous oils, greases and powders. Moist heat destroys the connecting resins in fiber optics. Reduction in light transmitted through a handpiece's fiber optic light orifices occurs after just a few autoclave cycles. Autoclaving can damage plastics. Chemiclaves are normally operated at even higher temperatures than autoclaves.

Dry heat has its own problems. High temperature dry heat sterilization is entirely unsuited for fabrics, plastics and rubber goods. Dry heat also destroys metal and solder joints and dulls blades. Dry heat destroys the temper of metal instruments. Dry heat may not penetrate jellies, greases and anhydrous oils. Dry heat may sterilize powders but only after long exposure.

Ethylene oxide $C_2H_4O$ can sterilize many heat sensitive items without damaging them. However, sterilizing with $C_2H_4O$ has its own unique set of problems. $C_2H_4O$, a derivative of petroleum hydrocarbons and a flammable carcinogen, presents what are really unacceptable risks for workers and patients, including a risk of explosions. Ethylene oxide sterilizers are also large, cumbersome, difficult to use and prohibitively expensive outside of the hospital environment. Additionally, and as previously discussed, $C_2H_4O$ sterilization takes even longer than moist and dry heat sterilization, substantially longer. Exposures to treatment for at least several hours and often overnight are required. Significant additional time is also needed to dissipate residuals of this hazardous chemical from sterilized materials that have absorbed it. Hazardous quantities of ethylene oxide persist in plastics, rubbers, and fabrics for several hours, and even days following treatment. 128 hours after a 16 hour treatment with ethylene oxide, leather was found to have still retained 10–18% of the absorbed gas.

The extended times required for moist heat, dry heat and ethylene oxide sterilization burden the economy. Surgical and other productive tools are removed from use while being sterilized. A complete autoclave cycle, from preparation with ultrasonic scaling to post treatment drying and cooling, typically takes 1 hour. Chemiclaves, with their slow penetration, must be operated for even longer cycles than autoclaves in order to sterilize. Dry heat furnaces are typically operated for 2 hours at 320° F. to sterilize. While higher dry heat temperatures can shorten the sterilization time, the risk of damage to the materials being sterilized increases proportionately. Even carbon steel instruments are heat treated for hardness and should not be routinely sterilized at temperatures above 325° F. Ethylene oxide sterilization requires exposure of materials for at least several hours and often overnight. The art of surgical instruments sterilization is discussed at length in a text entitled *Principals and Methods of Sterilization in Health Sciences,* Second Edition, John J. Perkins author, Copyright 1956 and 1969, Charles C. Thomas publisher, Springfield, Ill.

If ozone could be perfected as a sterilant, it might then overcome many of these disadvantages of other methods of sterilization.

Consider the sterilization of dental drill handpieces when evaluating the advantages that $O_3$ sterilization might present. These precision instruments, costing about $800.00 each, turn at between 380,000 to 450,000 rpm. They have a turbine containing many component parts with precision tolerances, like spindles or shafts, two sets of bearings (retainer ring, ball bearings, inner and outer race) and an impeller. The tolerances for these parts are measured in millionths of an inch. Internal hand piece components are more prone to malfunction after frequent sterilization at high temperature, M. R. Wirthlin, Jr., I. L. Shkiair, R. A. Northerner, S. W. Shelton, and G. L. Bailey *The Performance of Autoclaved High-Speed Dental Handpieces* Journal of the American Dental Association, 103:584–587. The instruments can only withstand so many autoclave cycles before requiring repair or replacement.

Because of this, for a long time, dental surgeons preferred to "cold sterilize" these hand pieces, that is, to actually disinfect them by washing them with germicidal solutions, normally plain ethyl alcohol, which is not effective against all dried viruses, various glutaraldehyde solutions, like Cidex 7 and Vitacide, (thee generics are reportedly 20% ineffective due to a lack of standardized concentration), and iodine detergent scrubs at 1% concentration. This process was woefully inadequate for preventing the transmission of disease from the treated handpieces.

During clinical procedures, blood and other materials can be drawn deep into the pneumatically operated handpieces through their seals and the burr cooling air and water outlets. When the pneumatically powered handpieces are turned off after a surgical procedure, a condition of partial vacuum, occurring in the water and air lines, draws blood and other materials deep into the pieces. Considering the many lumens and crevices and possible diffusion barriers contained in the handpieces, surface treatment of the handpieces afterwards is, by itself, highly unlikely to deliver the germicidal solution to all pathogenic inoculum, especially those pathogens located in the handpiece interiors. When the handpieces are reused, they spray the still infected blood, amalgam, and pathogens into the next patient's surgical and other wounds. The risks of patient-to-patient cross infection, especially with blood borne viruses like Hepatitis A or B and HIV virus is quite real. This risk was noted by researchers Foley and Gutheim as early as 1956, F. E. Foley and R. N. Gutheim *Serum Hepatitis Following Dental Procedures: A Presentation of 15 Cases, Including Three Fatalities* Annals of Internal Medicine, 45:369–380, 1956. See also D. L. Lewis and R. K. Boe *Cross-Infection Risks Associated with Current Procedures for Using High-Speed Dental Handpieces* Journal of Clinical Microbiology, Volume 30, Number 2, February, 1992, pp 401–406 and D. Lewis. M. Arens, S. Appleton, K. Nakashima, J. Ryu, R. Boe, J. Patrick, D. Watanabe and M. Suzuki *Cross-Contamination Potential With Dental Equipment* Lancet, Volume 340, Nov. 21, 1992, pp 1252–1259. Some evidence exists that pathogenic endospores, which are drawn into the handpieces, may even survive autoclaving, S. Edwardsson, G. Svensater, and D. Birkhed *Steam Sterilization of Air Turbine Handpieces* Acta odonttol. Scand. 41:321–326, 1983. Also, some germicidal solutions may damage handpiece motors, are difficult to remove from inside the handpiece and/or present health concerns for workers and patients.

Both autoclaving and chemiclaving also damage the instruments. Studies demonstrate that metal ball bearings, rings and spheres are severely corroded after just 25 sterilization cycles, and nonmetallic parts like the phenolic resin retainers darken and become brittle, Emma Angelini *Influence of Sterilization on the Corrosion Resistance of High-Speed Dental Handpieces* Quintessence International, Volume 23, number 3, 1992, pp 215–222. Oiling regimens can reduce and delay these effects, but only to an extent, (ibid). Autoclave heat is not only sufficient to directly damage these stainless steel handpieces, it expands the precision, rotating bearings in these relatively expensive machines. While these instruments can cool to the touch and be re-used within 20 minutes after sterilization, all parts are not completely cooled to room temperature and contracted to original dimensions in this time. Considering the handpieces are used in rotating dental operatories where dentists tend to different patients approximately every 20 minutes, dentists, even those owning several sets of instruments, cannot allow for the lengthy cooling times actually required for the bearings to contract to their original dimension before the handpieces must be re-used. The expanded moving parts are damaged by grinding into other parts each time that the dentists are obliged to re-use the instruments before they have completely cooled. After several sterilizing cycles, the handpieces are ruined. Many of the above problems are only exasperated and additional damage to rubber and plastic parts created by higher temperature dry heat sterilization. This provides strong motivation for dental surgeons to not sterilize handpieces.

Autoclaving also requires significant time. Ten minutes are required for preparation of the handpieces for autoclaving by ultrasonic scaling and cleansing. While only 20 minutes exposure to the autoclave steam is required to sterilize, this cycle time is extended to 45 minutes when time is allowed for loading, pressurizing, depressurizing and unloading the autoclave chamber. Five additional minutes are required to dry the sterilized handpieces. Fifteen minutes more must elapse before the pieces are cooled enough to handle (much more time would be required if the pieces were allowed to cool long enough for their heat-expanded parts to contract to their original dimensions). The entire autoclave sterilization process takes a minimum of 75 minutes. Dentists must outlay additional capital for several sets of dental instruments in order to compensate for this down time. Dentists, who heat sterilize hand pieces rather than wiping them down with germicidal solutions, must possess between 15 and 20 handpieces (a $12,000 to $16,000 capital outlay), rather than 3 or 4, to permit an uninterrupted patient schedule. Moreover, this capital outlay is quickly lost as the result of the instruments damaged by heat sterilization. These possibly unnecessary added costs are passed onto the consumer in the form of increased health care costs. This disadvantage is only exasperated by dry heat, gas sterilization, and treatment with germicidal solutions, where the ADA guidelines specify an immersion in the solutions for 16 hours or more, Emma Angelini *Influence of Sterilization on the Corrosion Resistance of High-Speed Dental Handpieces* Quintessence International, Volume 23, Number 3, 1992, pp 215–222.

Moreover, heat of any type also breaks down the handpieces lubricating oils to gummy residues. These residues throw the handpiece turbines out of balance at high rpm. Burrs jiggle, lose concentricity of rotation and parts wear. Drill speeds are reduced after just a few autoclave cycles. Additionally, the detergents used for wipe down cleanings and during ultrasonic scaling, react with and breakdown the oils lubricating the handpieces' moving parts, and detergent residues, as well as, oil residues (gums and resins) can also bind the pieces' working parts. Detergents begin to react with nylon retainer rings at 135° C., and every 10 degree increase in temperature above 135° C. doubles the rate of these damaging reactions.

An ozone treatment perfected to sterilize these handpieces could overcome the two main concerns that the dental surgeon has with handpiece sterilization, that sufficient numbers of handpieces to meet patient scheduling needs will not be available because of sterilization down time and that equipment failures will proliferate as a result of frequent heat sterilizations. Ozone treatment is most effectively accomplished at temperatures below 100° C., so heat effects should not result in the handpiece damage described in the proceeding paragraphs, and ozone's contact oxidation should sterilize much more rapidly than steam under pressure. Heat from pressurized steam kills bacterial and viral cells by denaturing their proteins, that is by destroying the functional structure of the proteins. This requires time for the protein's polypeptide chains to be sufficiently agitated thermally to disturb the residual charges causing the chain to fold back upon itself. Dry heat, which destroys bacteria and viruses by very slow oxidation (burning), is even slower as a sterilizer than pressurized steam. Ethylene oxide, an alkylating agent, sterilizes even more slowly than dry heat. With $O_3$, ultrasonic scaling as a preparation method may be unnecessary, as the oils, jellies and soils, that must be removed prior to heat and ethylene oxide sterilization, interfere with the sterilization process and may hamper $O_3$ sterilization. Also, the stainless steel used to make dental handpieces is very resistant to $O_3$ breakdown. Unlike moist heat and some germicidal solutions, $O_3$ is unlikely to either disturb or prevent the formation and/or repair of the chromium oxide layers, that is oxide films, which provide strong resistances to corrosion of these high carbon steels. Like ethylene oxide, $O_3$ can safely sterilize heat sensitive materials. Unlike ethylene oxide, $O_3$ leaves no hazardous residues. $O_3$ in atmosphere quickly reverts to the benign gas $O_2$, leaving no hazardous or otherwise detrimental residues. $O_3$ will react with, breakdown, and sterilize hand piece oils, gums, fat deposits, and potentially machine binding scums. As with autoclaving, re-oiling the hand pieces after their sterilization may be necessary.

SUMMARY OF THE INVENTION

The present invention perfects the use of ozone as a sterilant for many classes of surgical instruments which are at least partially metallic, by modifying the conventional ozonator apparatus. The three features of the new apparatus/method are the connection of a voltage carrying part of the instrument to be sterilized as the electrode of an ozone generating cell, which employs a glow discharge to produce $O_3$ from $O_2$, no solid dielectric existing between opposed electrodes in the ozone generating cell and means, other than cooling by forcing fluids, for maintaining the temperature of this electrode below 500° C.

Ozone produced is thereby localized about voltage carrying and any non-voltage carrying parts of the electrode connected instrument. The control of electrode heating helps to maintain the increasing atmospheric concentration of the ozone, which will however eventually reach a natural limit at which the rates of $O_3+O=2O_2$ and $O+O=O_2$.

The apparatus/method described herein includes means for controlling local heating of the chance electrode configuration where the instrument to be sterilized is connected at least periodically as the negative electrode and no solid dielectric exists between opposed electrodes in the ozone generating cell. This helps to avoid the avalanche of the ozone generating glow discharge into an unproductive arc, that is a glow to arc transition.

Consider the geometry as simplified in FIGS. 2a)-2d). FIG. 2a) shows two flat plates at different voltages. There results a uniform field between the plates of magnitude $E_0=V/d$ where V is the difference in potential between the plates and d is the plate separation. This is the standard configuration for elementary capacitor problems. Now, suppose there is an imperfection to the smoothness of one of the surfaces as in FIG. 2b). The imperfection may represent an irregularity of the surface of the object to be sterilized or a contaminant and may be approximated as a hemisphere added to the surface. Poisson's Equation gives us the solution for the potential in this modified case, as well as the charge distribution and the electric field. The potential, $\phi$, is found from $\nabla^2 \phi = -4\pi_\alpha$. This leads to $\phi(r,\theta)=-E_o r \cos\theta + E_o a^3/r^2 \cos\theta$ for location between the plates. The resultant charge density on the plate shown in FIG. 2c) is $\sigma(\theta)=E_o/4_\pi(1-a^3/r^3)$ and on the imperfection the surface charge density is $\sigma(\theta)=3E_o/4_\pi \cos\theta$ giving an electric field of $E_r=E_o \cos\theta + 2E_o a^3/r^3 \cos\theta$ $E\theta=-E_o \sin\theta+E_o a^3/r^3 \sin\theta$ A+r=a (along the surface of the imperfection), this is $E=E_r=3E_o \cos\theta$.

The geometry periodically forces a nearly uniform electric field with a very narrow range of field variation. At no time during the alternation can the electric field vary by more than a factor of 3 from this constant value. There is no tendency for a glow to arc transition to occur from a field enhancement at an irregular surface. The glow discharge is rendered more stable. When the smooth surfaced plate acts as an anode, the electric field distribution provides the necessary accelerating field everywhere over a cathode object for production of ultraviolet light and charged particles with energies sufficient to sterilize on impact with the surface. The slightly enhanced field at a surface irregularity caused by a contaminating microbe will rapidly disappear as the enhanced field destroys the microbe.

The apparatus and method of the disclosed embodiment are accomplished in a chamber at subatmospheric pressure. Accomplishment at subatmospheric pressure produces UV light which increases $O_3$ production. In addition to the UV irradiation and soft X-rays, electron and/or ion bombardment of the electrode-connected instrument will occur in the ozone generating cell operated at subatmospheric pressures. These effects, which are themselves known to kill microbes, will compliment the antimicrobial ozone treatment of the instrument. UV irradiation (electromagnetic irradiation in the 2000 to 3000 angstrom range, particularly at 2537 A) is a known germicidal. $O_3$ reactions within the generating cell also produce germicidal chemicals such as nitrous oxides, nitronium perchlorate, and nitric acid, which all aid the antimicrobial ozone treatment. If moisture is present, $O_3$ may be photochemically decomposed by continued UV irradiation and the strong disinfectant and bleaching agent, hydrogen peroxide $H_2O_2$, produced as a byproduct. As to electron and ion bombardment, energy absorption as low as $10^5$ to $10^6$ reps is known in the literature to be lethal to single microorganisms. One rep denotes an energy absorption of $O_3$ ergs per gram of tissue. Accomplishing the method at subatmospheric pressure also limits the movement by convection currents of $O_3$ from the instrument being sterilized.

The apparatus and method of the disclosed embodiment provide control means which prevents the glow discharge from initiating before a predetermined subatmospheric pressure is reached, but which allows the glow discharge to continue if the pressure thereafter increases within a predetermined range. Current conducting from an electrode at too high a pressure risks incomplete disinfection. However, initiation of the glow discharge causes out gassing which can briefly raise the pressure of a 1.25 gallon chamber as much as 300 millitorr while the now heated electrode sustains the glow discharge at essentially the same intensity. It is undesirable for the ozonator to trip off during the out gassing.

In the preferred embodiment of the invention disclosed herein, objects to be sterilized are connected as both positive and negative electrodes of the ozone generating cell and the cell is powered by an alternating current. This configuration significantly improves the efficiency of the process from the standpoint of time and energy usage. There is no solid dielectric between the electrically opposed plates in the cell which is operated at subatmospheric pressure. In this manner, electron and ion bombardment aids the ozone disinfection of both the electrodes within the cell. This configuration may be compared to typical prior art ozonator cells which operate at atmospheric pressure or above and require a dielectric between the cell's electrodes as shown in prior art FIGS. 4a through 4d.

BRIEF DESCRIPTION OF THE DRAWINGS

The aforementioned objects and advantages of the present invention, as well as additional objects and advantages thereof, will be more fully understood hereinafter as a result of a detailed description of a preferred embodiment when taken in conjunction with the following drawings in which:

FIG. 2, comprising FIGS. 2a through 2d, is a simplified field diagram of two plates having a difference in electrical potential there between;

FIG. 3, comprising

FIG. 4, comprising

DETAILED DESCRIPTION OF PREFERRED EMBODIMENT

Figure 1:
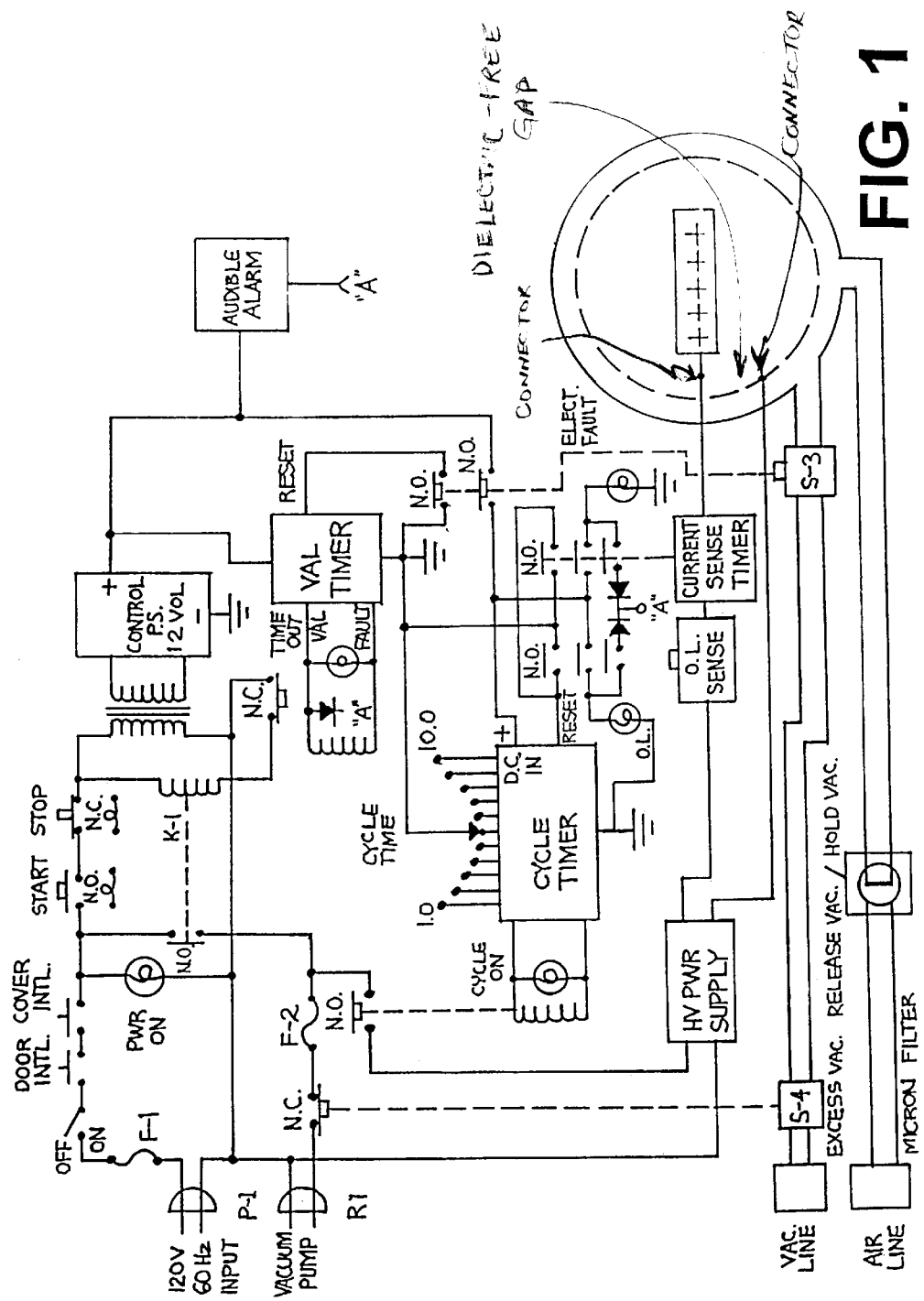
FIG. 1 is a schematic diagram of a preferred embodiment of the invention.
Figure 2A:
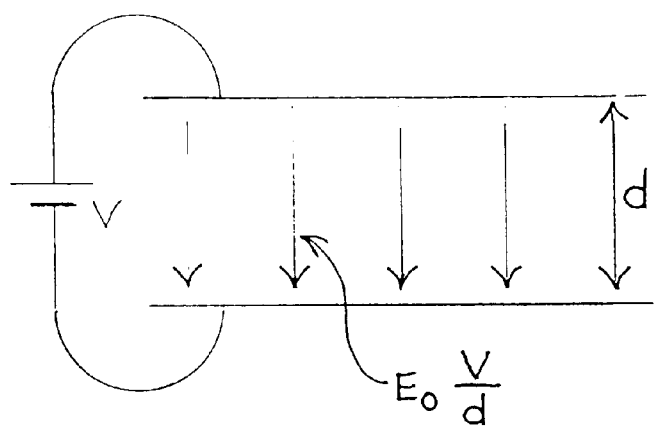
Figure 2B:
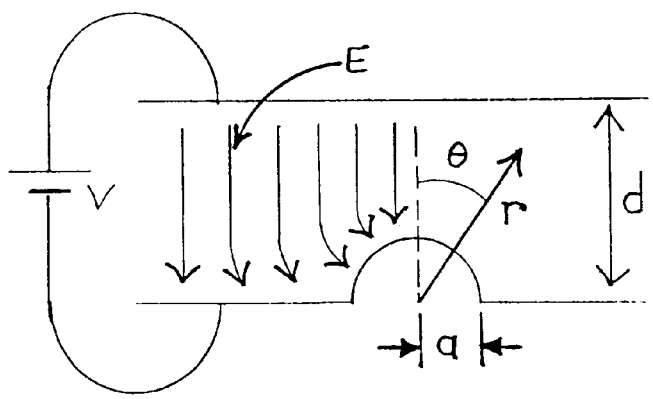
Figure 2C:
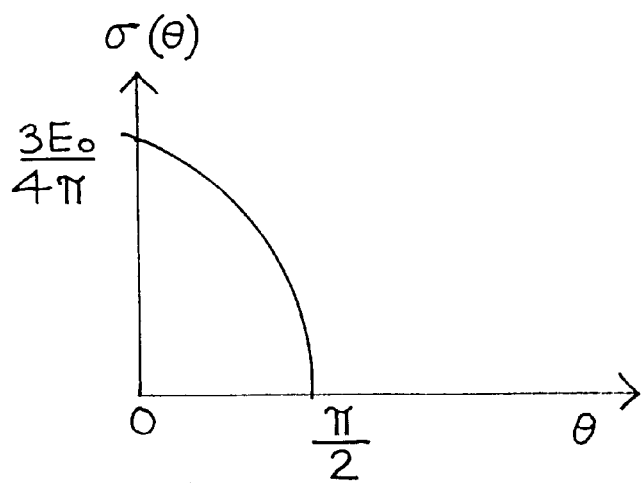
Figure 2D:
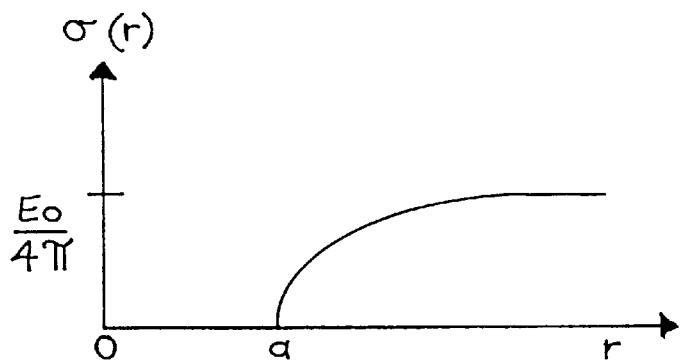
Figure 3A:
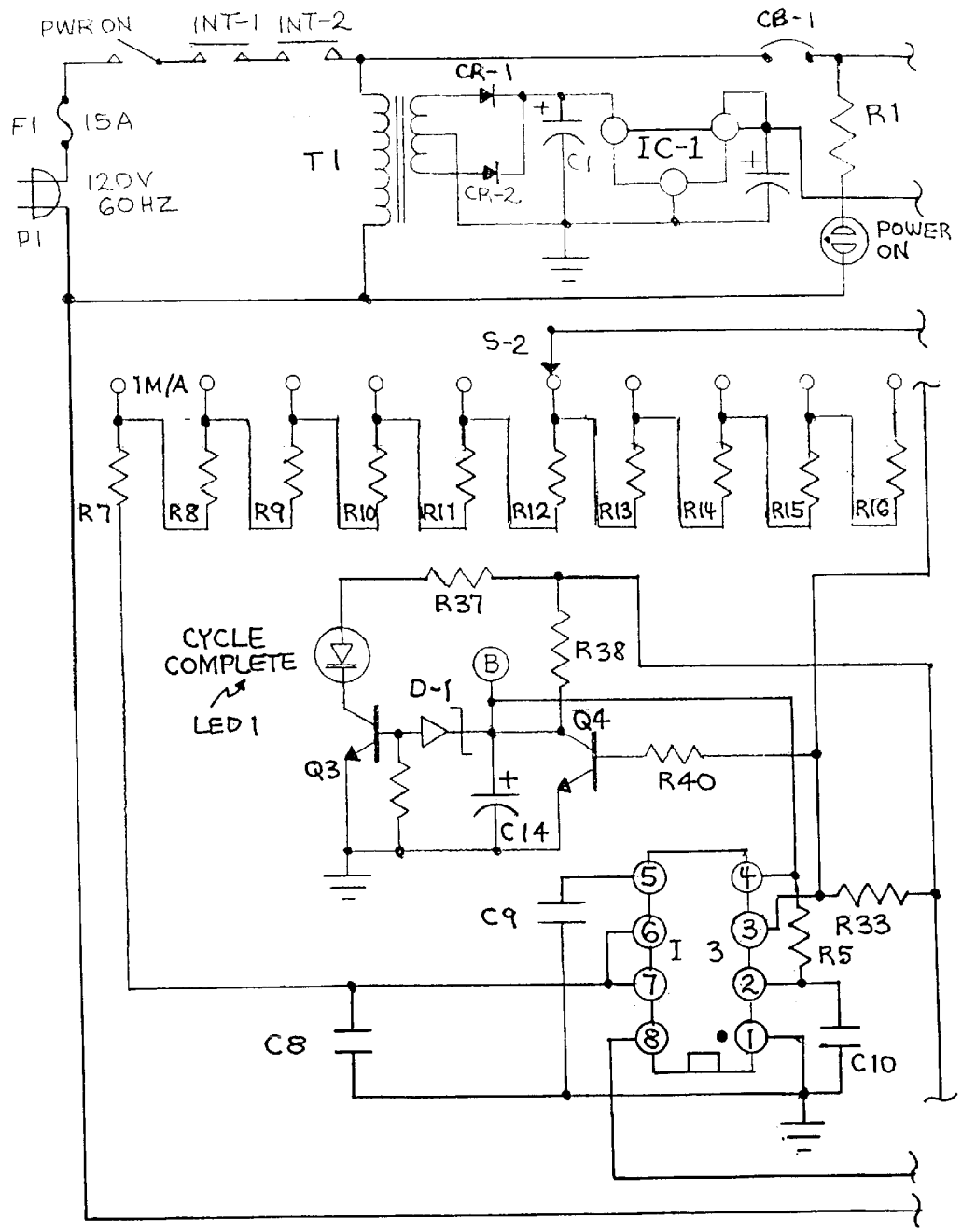
FIGS. 3a, 3b and 3c, is a schematic diagram of the logic controller circuitry of the preferred embodiment.
Figure 3B:
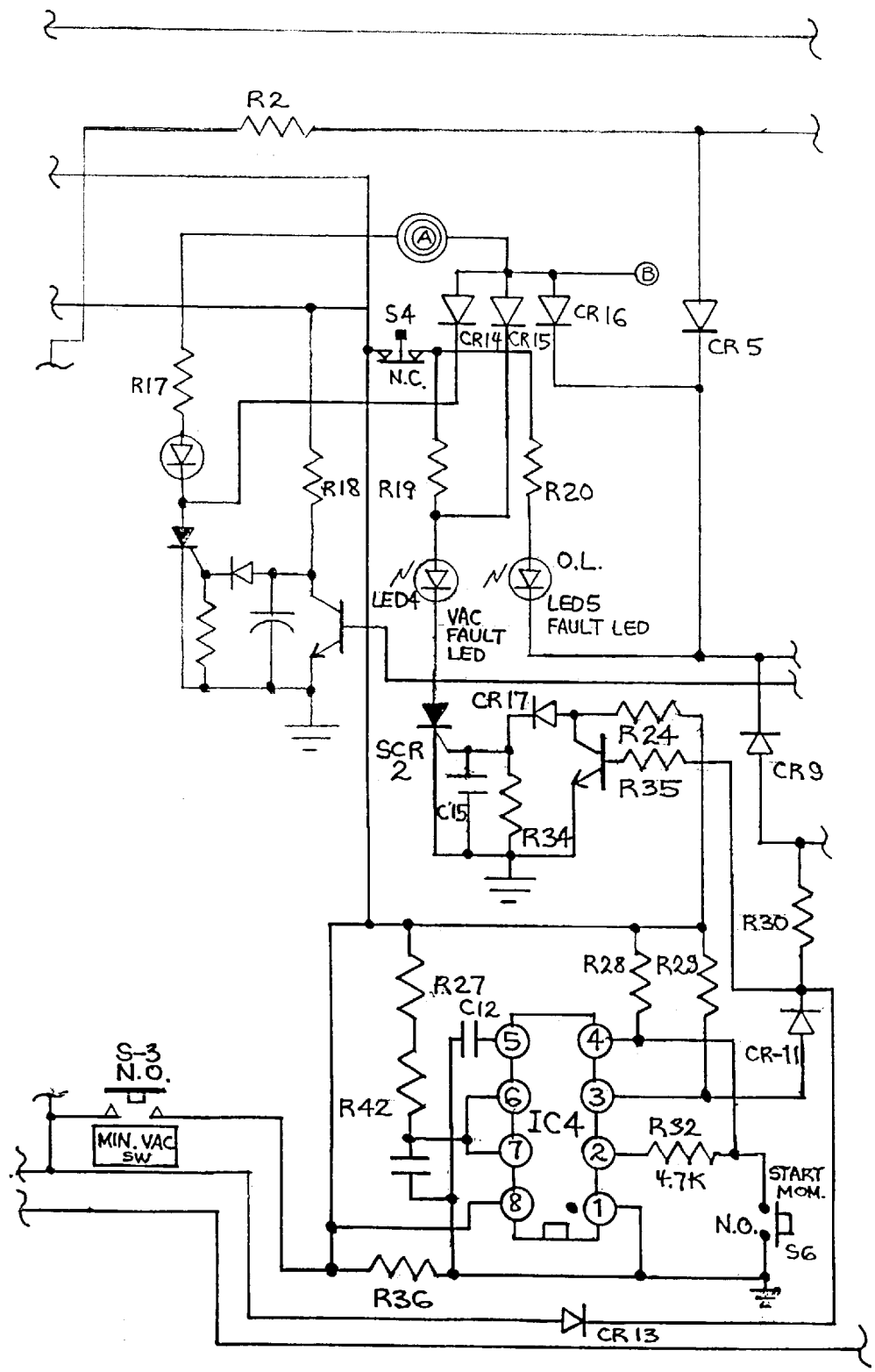
Figure 3C:
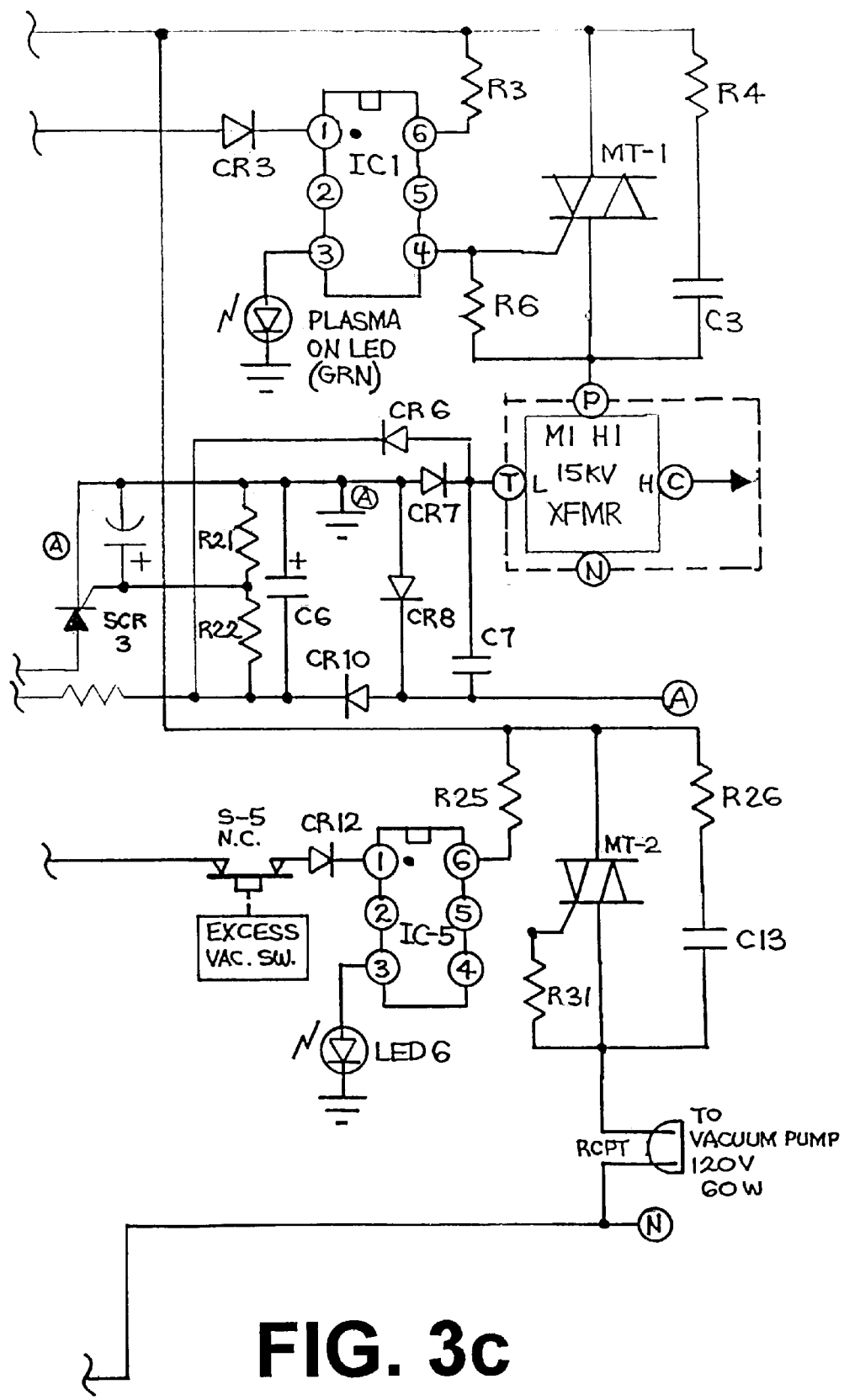
Figure 4A:
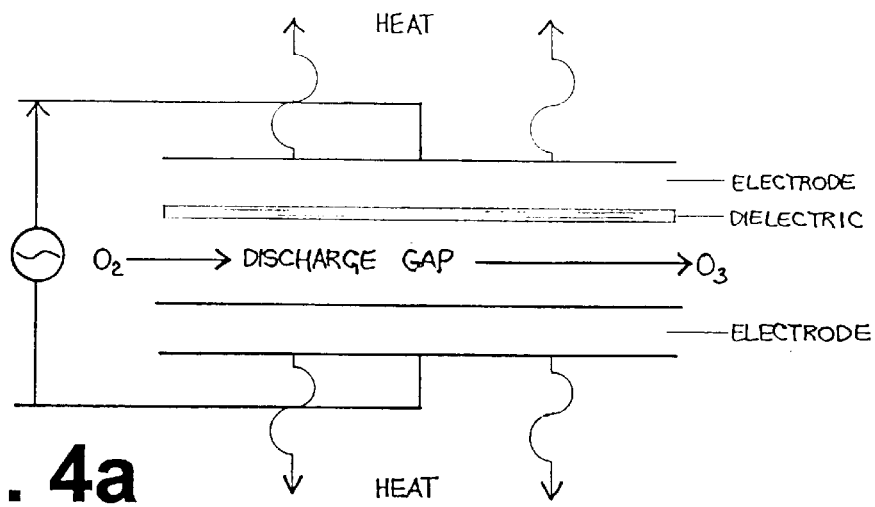
FIGS. 4a through 4d, illustrates operation of typical prior art ozonator cells.
Figure 4B:
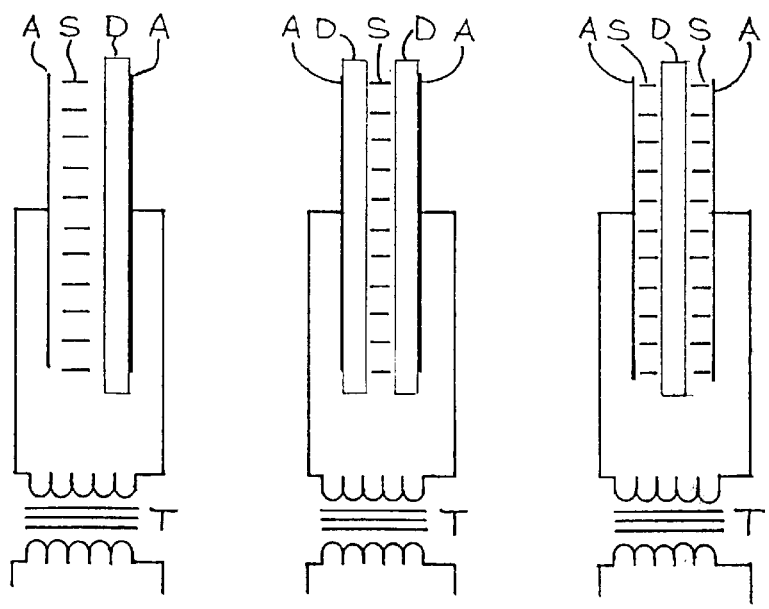
Figure 4C:
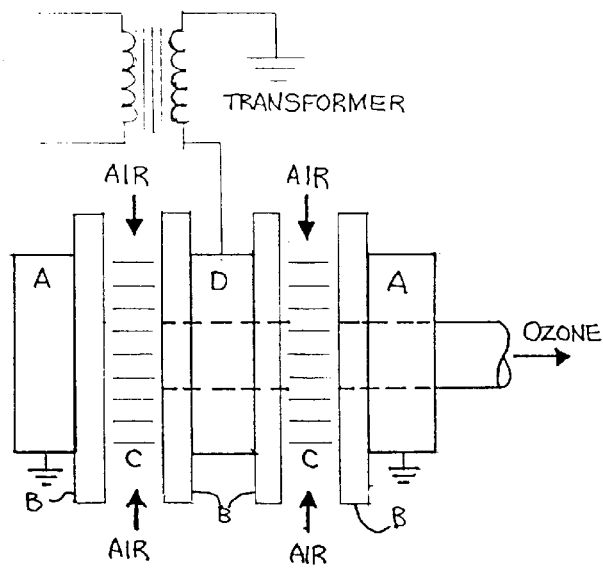
Figure 4D:
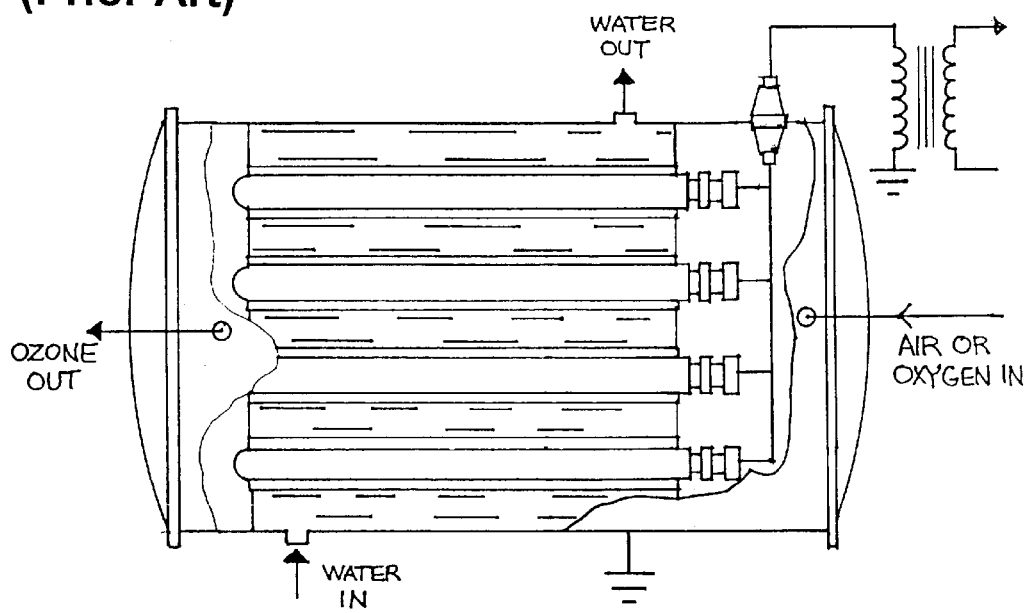

In the preferred embodiment shown in FIG. 1, within a 4.7 L (1.25 gallon) Nalgene bell jar (Fisher part No. 01-060A) (13) having a 17 cm O.D.×24 cm H (6⅝"×9⅜") (or any similarly specified chamber) and a 19 cm (7½") O.D. gasket, two electrodes (9 & 10) are mounted on the surface of a common ceramic dielectric with a minimum air gap of 0.5 cm between them. One electrode (9) is an uninsulated 7 cm long steel re-bar tie wire, approximately 16 AWG. This electrode is centered within an 18 cm long 23 gauge ¼" steel hardware cloth or diamond lathe cylinder having a diameter of 5 cm. The diamond lathe cylinder serves as the second electrode (10). 30 AWG magnet wire (14) with varnish insulation connects each electrode to an opposed pole of a France former reactance transformer, catalogue number 15060P, serial number 0395, with a primary specified for 120 V, 60 HZ, and 890 VA and a secondary specified for 15,000 VAC and 60 ma. This gaseous tube transformer is manufactured by France, a division of Scott Feltzer Co., Fairview, Tenn. 37062. Any similarly specified transformer will suffice. The 30 AWG magnet wires exit the bell jar between its neoprene gasket and its vacuum plate. The vacuum plate's tubing connection is connected to the intake of a Fast Vac DV-85 deep vacuum pump, model YQC48C17D380A, part number 10085-133, specified at 85 liters/minute and manufactured by JB industries, Inc., Aurora, Ill. 60507 (15). Any similarly specified pump will suffice. A dental drill handpiece to be sterilized is connected as an electrode by inserting the 7 cm re-bar tie wire (9) into one of the handpiece's lumens. Logic control circuitry, described in more detail in conjunction with FIG. 3 and Table 1, is in communication with the power feeds for both the neon transformer and/or the oil pump, pressure sensors on the vacuum line, and current sensors on the neon transformer's secondary.

TABLE 1

CONTROLLER PARTS LIST

| ITEM | CIRCUIT DESIGNATION | PART NUMBER | DESCRIPTION | MANUFACTURER |
|---|---|---|---|---|
| 1 | K1 | PM17DY | 4 PDT, 25 A RELAY 12 VDC COIL | POTTER BRUMFIELD |
| 2 | RCDT | 17252 | INPUT RECEPT. | BELDEN |
| 3 | RELAY COVER | 350203 | RELAY COVER | POTTER BRUMFIELD |
| 4 | F1 HOLDER | 345913A | FUSE HOLDER 3AG | LITTLE FUSE |
| 5 | F1 | 313020 | FUSE 20 A 3AG SB | LITTLE FUSE |
| 6 | LINE CONN. | 17504 | 6' LINE CONN. | BELDEN |
| 7 | S-1 | C222J125205POF | ON-OFF SW | C & K |
| 8 | INT-1 | BA-2RQ1-A2 | 20 A INTERLOCK SW | MICROSWITCH |
| 9 | T-1 | DSW-432 | 32 VCT 0.1888 A TRANSFORMER | STANLOR |
| 10 | IC-1 | UA7812CKC | 12 V 1.5 A REG +9% | T1 |
| 11 | IC-2 | NE555 | TIMER | T1 |
| 12 | IC-3 | MC1747CL (CP2) | DUAL UP-AMP | MOT |
| 13 | SCR-1 | 2N5061 | SENS. GATE SCR 0.8 A | MOT |
| 14 | C2–C3–C9 | UKB1E470KPA | 47 MFD 25 V CON LEAKAGE CAP | NICHIKON |
| 15 | C1 | 1H471MHA | 470 MFD 50 V CAP | NICHIKON |
| 16 | C-6 | 5HK550 | 0.05 MFD 500 V CAP | SPRAGUE |
| 17 | C4–C5 | HY820 | 0.01 MFD 25 V CER CAP | SPRAGUE |
| 18 | CR1–CR4 | IN4001 | 1 A 5UV RECT. DIODE | MOT |
| 19 | Q-1 | TIP-33C | 10 A 100 V NPN X515TON | MOT |
| 20 | R1 | HB5001 | 50 r 2w RESISTOR 10% | A-B |
| 21 | R2–R3 | EB2715 | 270 r ½w 5% RESISTOR | A-B |
| 22 | R4, R8 | CB4725 | 4.7 Kr ¼w 5% RESISTOR | A-B |
| 23 | R5 | CB4755 | 4.7 MEGr ¼w 5% RESISTOR | A-B |

TABLE 1-continued

CONTROLLER PARTS LIST

| ITEM | CIRCUIT DESIGNATION | PART NUMBER | DESCRIPTION | MANUFACTURER |
|---|---|---|---|---|
| 24 | R6 | CB3335 | 33 Kr ¼w 5% RESISTOR | A-B |
| 25 | R7 | 3059P 10R | 10Kr CERMET 22 TURN POT. | BOURNES |
| 26 | C7, C8 | TST22 | 22 OPS 100 V DISC. CAP. | SPRAGUE |
| 27 | S-2 | 9001D1A1OMO1 | N,O, MMOMENTARY 20 AM 10 COM | SQUARED |
| 28 | L-1 | VACUUM ON | AMBER NEON LIGHT | RADIO SHACK |
| 29 | L-2 | STERILIZING | RED NEON LIGHT | RADIO SHACK |
| 30 | R-4 | CB4735 | 47 Kr ¼w 5% | A-B |
| 31 | D-1 | IN5225B | 3.0 V 0.5 W ZENER DIODE | MOT |
| 32 | EM1 | 20VK1 | 20 AMP EMI FILTER | CURCOM |

Figure 5:
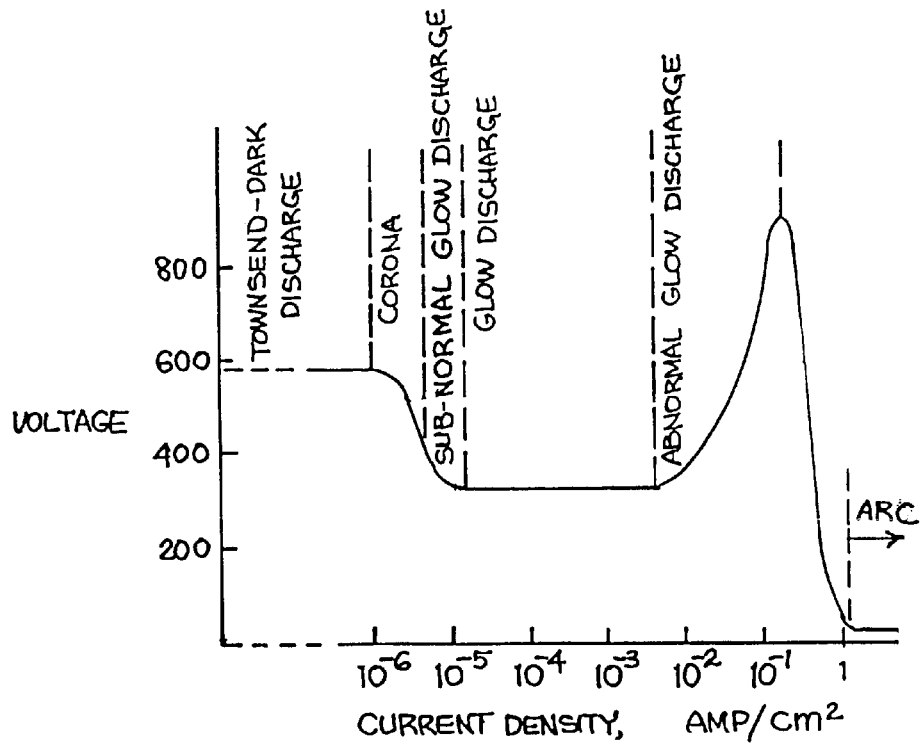
FIG. 5 is a graphical illustration of voltage versus current density showing various conditions of discharge that result.

After throw switch (3) is closed, the vacuum pump begins to draw atmosphere from chamber (1) when momentary switch (2) is depressed and latch circuit (4) activates. Vacuum switch (5) closes at a subatmospheric pressure of 1000 millitorr and activates the glow discharge cycle timer (6) which closes switch (7) providing power to the primary of high voltage transformer(8) for 10 minutes. Power from the secondary step up transformer (8) causes an abnormal glow discharge to alternately envelope all voltage carrying parts of electrode (9), which includes the voltage carrying parts of the instrument to be sterilized, and electrode (10) as each periodically acts as the cathode. This is both an unusual configuration and power per $cm^2$ of electrode surface for an ozonator. Other corona discharge ozonator cells have gas feed pressures at or above atmosphere and have their opposed electrodes separated by a solid dielectric (usually glass) with 2–3 mm air gaps on each side of the dielectric between the dielectric and the electrode plates. Operated normally at about 250 W per cubic foot of electrode plate, the ozonators can only produce a corona glow, the weakest of the glow discharges. Without the dielectric, an arcing discharge occurs between the plates. Normal glow discharges required more power per $cm^2$ of electrode surface than corona glows. Abnormal cathode glows require even more power than normal glows. The abnormal cathode glow occurs at power levels just beneath those where the glow would progress into an arc discharge (see FIG. 5). The abnormal glow distributes to cover all voltage carrying surfaces of the cathode and is probably a capacitive effect. It is difficult to prevent this discharge from avalanching into an arc at field enhancement points or from hot spots on the cathode absent current regulation, hence the need to limit current via voltage drops in the reactance transformer. However, an abnormal glow is needed to produce UV radiation and ozone production about the entire cathode surface. It also allows complimenting antimicrobial electron and ion bombardment to occur on all electrode surfaces.

The intensity of the cyclic abnormal glow increases as does the temperature of the electrode. However, as indicated by Templistiks, the temperature of the dental handpiece electrode remains below 200° F. for about the first five minutes of discharge and does not reach 220° F. during a 10 minute discharge, see Tables 2, 3a & 3b below.

TABLE 2

| MARK NUMBER | MARK MELTS AT DEGREES (F.) |
|---|---|
| 1 | 125° |
| 2 | 150° |
| 3 | 175° |
| 4 | 200° |
| 5 | 225° |
| 6 | 250° |
| 7 | 275° |
| 8 | 300° |
| 9 | 325° |
| 10 | 347° |
| 11 | 392° |

TABLE 3A

| TIME IN MINUTES | TEMPERATURE IN DEGREES FAHRENHEIT |
|---|---|
| 1 | 125° |
| 2 | 175° |
| 3 | 175° |
| 4 | 175° |
| 5 | 175° |
| 6 | 200° (approximately) |
| 7 | 200° (approximately) |
| 8 | 200° (approximately) |
| 9 | 200° (approximately) |
| 10 | 215° (approximately) |

TABLE 3B

| TIME IN MINUTES | TEMPERATURE IN DEGREES FAHRENHEIT |
|---|---|
| 1 | 125° |
| 2 | 150° |
| 3 | 175° |
| 4 | 175° |
| 5 | 200° |
| 6 | 215° (approximately) |
| 7 | 215° (approximately) |
| 8 | 215° (approximately) |
| 9 | 215° (approximately) |
| 10 | 215° (approximately) |

After 10 minutes, switch (7) opens and the discharge is extinguished. Audible alarm (11) sounds. Throw switch (3)

is manually opened and the vacuum is turned off. Exhaust valve (12) is manually opened and air reintroduced into the chamber (1) until atmosphere is reached. The chamber is opened and a completely sterile dental drill handpiece is removed. Not just the ion bombarded, electron bombarded and irradiated voltage carrying handpiece components are sterilized, but the dielectric gaskets, rings, stoppers and oils are also sterile. Vacuum switch 16 disconnects power to pump (15) while pressure in chamber 1 exceeds a pressure 1000 millitorr plus an allowance for handpiece out gassing.

If a minimum vacuum of 1000 millitorr is not achieved in chamber within a predetermined time, then, vacuum timer (13) times out and opens switch (17) while energizing vacuum fault lamp (18). The power from the 120 VAC wall source is disconnected.

Efficient production of $O_3$ in typical ozonator cells, like the Lowther cell, requires means for cooling. Ozonators contain heat sinks and are commonly cooled by air or water as heat reduces $O_3$ production. 85% of energy used is lost to heat in these inefficient cells which would quickly heat to undesirable temperatures if not cooled. Typical ozonators also produce relatively large volumes of ozone in dehumidified (see earlier discussion of ozone reducing effects of moisture) pressurized air or $O_2$, about 1–10% by volume, as the ozone must be diffused to remote contaminants. With these ozonators, efficient $O_3$ production requires the rapid forced removal of $O_3$ produced. Otherwise, the $O_3$ production is naturally self limiting because as discussed earlier, the higher the $O_3$ concentration, the higher the rate of $O_3$ decomposition. The preferred embodiment, here described, is compact and does not require these cumbersome means for cooling the electrodes or dehumidifying and forcing movement of the large volumes of feed air or gas.

Tables 4–8 show the results of 27 separate experiments. In each experiment, 3 hand pieces were ozonated in an experimental apparatus as described above and compared against a control; a total of 81 experimental handpiece treatments.

TABLE 4

| RUN NO. | FLASK NO. | Time in Minutes | DAY 1 | DAY 2 | DAY 3 | DAY 4 | DAY 5 | DAY 6 | DAY 7 | Comment |
|---|---|---|---|---|---|---|---|---|---|---|
| 1 | 1 | Control | G | — | — | — | — | — | — | A |
| 1 | 2 | 4 | G | — | — | — | — | — | — | A |
| 1 | 3 | 3 | G | — | — | — | — | — | — | A |
| 1 | 4 | 2 | G | — | — | — | — | — | — | A |
| 2 | 1 | Control | G | — | — | — | — | — | — | A |
| 2 | 2 | 4 | G | — | — | — | — | — | — | A |
| 2 | 3 | 3 | G | — | — | — | — | — | — | A |
| 2 | 4 | 2 | G | — | — | — | — | — | — | A |
| 3 | 1 | 5 | G | — | — | — | — | — | — | A |
| 3 | 2 | 5 | G | — | — | — | — | — | — | A |
| 3 | 3 | 5 | G | — | — | — | — | — | — | A |
| 3 | 4 | 5 | G | — | — | — | — | — | — | A |
| 4 | 1 | 5 | G | — | — | — | — | — | — | B |
| 4 | 2 | 5 | G | — | — | — | — | — | — | B |
| 4 | 3 | 5 | G | — | — | — | — | — | — | B |
| 4 | 4 | 5 | G | — | — | — | — | — | — | B |
| 5 | 1 | 6 | G | — | — | — | — | — | — | A |
| 5 | 2 | 6 | G | — | — | — | — | — | — | A |
| 5 | 3 | 6 | G | — | — | — | — | — | — | A |
| 5 | 4 | 6 | G | — | — | — | — | — | — | A |
| 6 | 1 | 6 | G | — | — | — | — | — | — | B |
| 6 | 2 | 6 | G | — | — | — | — | — | — | B |
| 6 | 3 | 6 | G | — | — | — | — | — | — | B |
| 6 | 4 | 6 | G | — | — | — | — | — | — | B |
| 7 | 1 | Control | G | — | — | — | — | — | — | A |
| 7 | 2 | 8 | G | — | — | — | — | — | — | A |
| 7 | 3 | 8 | G | — | — | — | — | — | — | A |
| 7 | 4 | 8 | G | — | — | — | — | — | — | A |
| 8 | 1 | Control | G | — | — | — | — | — | — | B |
| 8 | 2 | 8 | G | — | — | — | — | — | — | B |
| 8 | 3 | 8 | G | — | — | — | — | — | — | B |
| 8 | 4 | 8 | G | — | — | — | — | — | — | B |
| 9 | 1 | Control | G | G | G | G | G | G | G | B |
| 9 | 2 | 10 | NG | NG | NG | NG | NG | NG | NG | B |
| 9 | 3 | 10 | NG | NG | NG | NG | NG | NG | NG | B |
| 9 | 4 | 10 | NG | G | — | — | — | — | — | B |
| 10 | 1 | Control | G | — | — | — | — | — | — | A |
| 10 | 2 | 10 | G | — | — | — | — | — | — | A |
| 10 | 3 | 10 | G | — | — | — | — | — | — | A |
| 10 | 4 | 10 | G | — | — | — | — | — | — | A |
| 11 | 1 | Control | G | G | G | G | G | G | G | B |
| 11 | 2 | 10 | NG | NG | NG | NG | NG | NG | NG | B |
| 11 | 3 | 10 | NG | NG | NG | NG | NG | NG | NG | B |
| 11 | 4 | 10 | NG | NG | NG | NG | NG | NG | NG | B |
| 12 | 1 | Control | G | G | G | G | G | G | G | B |
| 12 | 2 | 9 | NG | G | — | — | — | — | — | B |
| 12 | 3 | 9 | NG | NG | NG | NG | NG | NG | NG | B |
| 12 | 4 | 9 | NG | G | — | — | — | — | — | B |
| 13 | 1 | Control | G | G | G | G | G | G | G | B |
| 13 | 2 | 10 | NG | NG | NG | NG | NG | NG | NG | B |
| 13 | 3 | 10 | NG | NG | NG | NG | NG | NG | NG | B |

TABLE 4-continued

| RUN NO. | FLASK NO. | Time in Minutes | DAY 1 | DAY 2 | DAY 3 | DAY 4 | DAY 5 | DAY 6 | DAY 7 | Comment |
|---|---|---|---|---|---|---|---|---|---|---|
| 13 | 4 | 10 | NG | NG | NG | NG | NG | NG | NG | B |
| 14 | 1 | Control | G | G | G | G | G | G | G | B |
| 14 | 2 | 9 | G | — | — | — | — | — | — | B |
| 14 | 3 | 9 | G | — | — | — | — | — | — | B |
| 14 | 4 | 9 | NG | NG | NG | NG | NG | NG | NG | B |
| 15 | 1 | Control | G | G | G | G | G | G | G | B |
| 15 | 2 | 9 | G | — | — | — | — | — | — | B |
| 15 | 3 | 9 | NG | NG | NG | NG | NG | NG | NG | B |
| 15 | 4 | 9 | NG | NG | NG | NG | NG | NG | NG | B |
| 16 | 1 | Control | G | G | G | G | G | G | G | B |
| 16 | 2 | 10 | NG | NG | NG | NG | NG | NG | NG | B |
| 16 | 3 | 10 | NG | NG | NG | NG | NG | NG | NG | B |
| 16 | 4 | 10 | NG | NG | Ng | NG | NG | NG | NG | B |

G = Growth of *Bacillus stearothermophilus*
NG = No growth
Experimental flasks terminated after growth occurred.
*A = Hand pieces dried with pressurized air only
B = Hand pieces dried with pressurized air followed by 15–20 minutes in 60° C. incubator

TABLE 5

| RUN NO. | FLASK NO. | Minutes To Draw Down | Plasma Exposure time in Minutes | DAY 1 | DAY 2 | DAY 3 | DAY 4 | DAY 5 | DAY 6 | DAY 7 |
|---|---|---|---|---|---|---|---|---|---|---|
| 20 | 1 | Control | Control | G | — | — | — | — | — | — |
| 20 | 2 | 12 | 10 | NG | NG | NG | NG | NG | NG | NG |
| 20 | 3 | 15 | 10 | NG | NG | NG | NG | NG | NG | NG |
| 20 | 4 | 12, 30 sec | 10 | NG | NG | NG | NG | NG | NG | NG |
| 21 | 1 | Control | Control | G | — | — | — | — | — | — |
| 21 | 2 | 13 | 9 | G | — | — | — | — | — | — |
| 21 | 3 | 12 | 9 | NG | G | — | — | — | — | — |
| 21 | 4 | 13 | 9 | G | — | — | — | — | — | — |

Hand pieces inoculated with *B. stearothermophilus* and dessicated prior to treatment.

TABLE 6

| RUN NO. | FLASK NO. | DRAW DOWN TIME IN MINUTES | DAY 1 | DAY 2 | DAY 3 | DAY 4 | DAY 5 | DAY 6 | DAY 7 |
|---|---|---|---|---|---|---|---|---|---|
| 22 | 1 | Control | G | — | — | — | — | — | — |
| 22 | 2 | 5 | NG | NG | NG | NG | NG | NG | NG |
| 22 | 3 | 5 | NG | NG | NG | NG | NG | NG | NG |
| 22 | 4 | 6 | NG | NG | NG | NG | NG | NG | NG |
| 23 | 1 | Control | G | — | — | — | — | — | — |
| 23 | 2 | 4 | NG | NG | NG | NG | NG | NG | NG |
| 23 | 3 | 6 | NG | NG | NG | NG | NG | NG | NG |
| 23 | 4 | 4 | NG | NG | NG | NG | NG | NG | NG |
| 24 | 1 | Control | G | — | — | — | — | — | — |
| 24 | 2 | 5 | NG | NG | NG | NG | NG | NG | NG |
| 24 | 3 | 5 | NG | NG | NG | NG | NG | NG | NG |
| 24 | 4 | 8 | NG | NG | NG | NG | NG | NG | NG |

Dental Hand pieces inoculated with *B. stearothermophilus* and sheep blood and then undessicated at 60° C. for 1½ hours prior to ten (10) minute treatment.
G = Growth of *Bacillus stearothermophilus*
NG = No growth
Experimental flasks terminated after growth occurred.

TABLE 7

| RUN NO. | FLASK NO. | DAY 1 | DAY 2 | DAY 3 | DAY 4 | DAY 5 | DAY 6 | DAY 7 |
|---|---|---|---|---|---|---|---|---|
| 25 | 1 | G | — | — | — | — | — | — |
| 25 | 2 | NG | NG | NG | NG | NG | NG | NG |
| 25 | 3 | NG | NG | NG | NG | NG | NG | NG |

TABLE 7-continued

| RUN NO. | FLASK NO. | DAY 1 | DAY 2 | DAY 3 | DAY 4 | DAY 5 | DAY 6 | DAY 7 |
|---------|-----------|-------|-------|-------|-------|-------|-------|-------|
| 25 | 4 | NG | NG | NG | NG | NG | NG | NG |
| 26 | 1 | G | — | — | — | — | — | — |
| 26 | 2 | NG | NG | NG | NG | NG | NG | NG |
| 26 | 3 | NG | NG | NG | NG | NG | NG | NG |
| 26 | 4 | NG | NG | NG | NG | NG | NG | NG |

Dental Hand pieces wiped with paper towelette and centrifuged at 3000 RPM for five (5) minutes prior to a ten (10) minute treatment.
G = Growth of *Bacillus stearothermophilus*
NG = No growth
Experimental flasks terminated after growth occurred.

TABLE 8

| RUN NO. | FLASK NO. | DAY 1 | DAY 2 | DAY 3 | DAY 4 | DAY 5 | DAY 6 | DAY 7 |
|---------|-----------|-------|-------|-------|-------|-------|-------|-------|
| 29 | 1 | G | — | — | — | — | — | — |
| 29 | 2 | NG | NG | NG | NG | NG | NG | NG |
| 29 | 3 | NG | NG | NG | NG | NG | NG | NG |
| 29 | 4 | NG | NG | NG | NG | NG | NG | NG |
| 30 | 1 | G | — | — | — | — | — | — |
| 30 | 2 | NG | NG | NG | G | — | — | — |
| 30 | 3 | NG | NG | NG | NG | NG | NG | NG |
| 30 | 4* | G | — | — | — | — | — | — |
| 32 | 1 | G | — | — | — | — | — | — |
| 32 | 2 | NG | NG | NG | NG | NG | NG | NG |
| 32 | 3 | NG | NG | NG | NG | NG | NG | NG |
| 32 | 4 | NG | NG | NG | NG | NG | NG | NG |
| 33 | 1 | G | — | — | — | — | — | — |
| 33 | 2 | NG | NG | NG | NG | NG | NG | NG |
| 33 | 3 | NG | NG | NG | NG | NG | NG | NG |
| 33 | 4 | NG | NG | NG | NG | NG | NG | NG |

*The handpiece shifted after the run began. The top of the handpiece came into contact with the cage disrupting the plasma field. No arcing was observed so the run was allowed to continue.

Innoculated with *B. stearothermophilus* and wiped with a paper towellete and centrifuged at 3700 RPM for five (5) minutes priot to ten (10) minute treatment.

Prior to being inoculated, each handpiece was sterilized by autoclaving at 121° C. for 15 minutes. A *B.Stearothermopholis* control was included In each sterilization cycle. Each piece was then inoculated by dipping in a commercial suspension of *B.Stearothermopolis* (SporAmpule Biological Indicator).

For some experiments, the experimental and control pieces were dried with forced air after inoculation. For some experiments, after inoculation, the experimental and control pieces were dried with forced air followed by 55–20 minutes desiccation in a 60° C. incubator. For some experiments, after inoculation, the experimental and control pieces were dried by desiccation in an incubator at 60° C. for 1½ hours. For some experiments, after inoculation, the experimental and control pieces were dried by desiccation at room temperature for one week. For some experiments, after inoculation, the experiment and control pieces were dried by centrifuging at 3000 to 3700 rpm for five minutes.

The experimental pieces were then ozonated. After the experimental treatment, both the control and experimental pieces were placed into a 1000 ml flask containing 500 ml of sterile Tryptic soy broth (TSB). The flasks were agitated so all handpiece surfaces might be exposed to the broth. The flasks were incubated at 56° C. for 7 days or until microbial growth was evident.

Forty-two of the experimental pieces were ozonated for 10 minutes after having been desiccated or centrifuged (not just dried with forced air). All but three of these forty-two pieces showed no *B.Stearothermopolis* growth after 7 days. All of the fourteen controls showed growth on the first day. Of the three experimental pieces showing growth, growth in one was clearly the result of an accident which extinguished the abnormal glow during treatment. In one of the other cases, growth occurred on the second day. This piece was ozonated at a subatmospheric pressure of 200 millitorr. In the other two cases, growth occurred on the forth day. This piece was ozonated at a subatmospheric pressure of 1000 millitorr. No explanation for these latter two failures is apparent.

The presence or absence of microbial growth was determined by visual evaluation (turbidity evident in the TSB) and Gram staining and microscopic examination of a slide sample for the presence of *B. Stearothermopolis*.

Table 9 shows growth after the first day for all eight experiment dental drill handpieces treated at approximately the same temperature with boiling water at atmosphere for ten minutes in an attempt to sterilize them. Table 10 shows growth after the first day for all six experiment dental handpieces subjected to a subatmospheric pressure of 200 millitorr alone for ten minutes in an attempt to sterilize them.

TABLE 9

| RUN NUMBER | FLASK NUMBER | TIME | DAY 1 |
|------------|--------------|------|-------|
| 19 | 1 | Control | G |
| 19 | 2 | 10 minutes | G |

TABLE 9-continued

| RUN NUMBER | FLASK NUMBER | TIME | DAY 1 |
|---|---|---|---|
| 20 | 1 | Control | G |
| 20 | 2 | 10 minutes | G |
| 20 | 3 | 10 minutes | G |
| 20 | 4 | 10 minutes | G |
| 21 | 1 | Control | G |
| 21 | 2 | 10 minutes | G |
| 21 | 3 | 10 minutes | G |
| 21 | 4 | 10 minutes | G |

TABLE 10

| RUN NUMBER | FLASK NUMBER | TIME IN MINUTES | DAY 1 |
|---|---|---|---|
| 18 | 1 | Control | G |
| 18 | 2 | 10 | G |
| 18 | 3 | 10 | G |
| 18 | 4 | 10 | G |
| 19 | 1 | Control | G |
| 19 | 2 | 10 | G |
| 19 | 3 | 10 | G |
| 19 | 4 | 10 | G |

G = Growth of *Bacillus stearothermophilus*
NG = No growth
Experimental flasks terminated after growth occurred.

Having thus disclosed a preferred embodiment of the invention, it being understood that various modifications, substitutions and additions are contemplated and that the scope hereof is limited only by the appended claims and their equivalents,

What I claim is:

1. An instrument sterilization apparatus for instruments having a metal part, the apparatus comprising:

an ozonator having high voltage spaced connectors configured to form an cathode and anode respectively, one of said connectors being attached to said instrument to form a glow discharge electrode from said metal part;

a dielectric-free gap between said spaced connectors; and a controller for regulating the application of voltage to said connectors for preventing a glow-to-arc transition and thereby promote ozone production within said chamber.

2. The apparatus recited in claim 1 wherein said controller is configured for modifying said voltage application to limit the temperature at said instrument during ozone production.

3. The apparatus recited in claim 1 wherein said controller is configured for reversing the polarity of applied voltage.

4. The apparatus recited in claim 1 further comprising an evacuatable chamber enclosing said connectors.

5. The apparatus recited in claim 4 further comprising a vacuum pump for reducing pressure in said chamber to subatmospheric.

6. The apparatus recited in claim 5 wherein said controller is configured for controlling applied voltage according to the subatmospheric pressure in said chamber to maintain a glow discharge between said connectors.

7. The apparatus recited in claim 1 wherein said one of said connectors attached to said instrument comprises a smooth surface which is larger than said instrument.

* * * * *